(12) United States Patent
Fraser et al.

(10) Patent No.: US 8,461,099 B2
(45) Date of Patent: Jun. 11, 2013

(54) FRAGRANCE MICROEMULSION COMPOSITIONS

(75) Inventors: Stuart Fraser, Cheshire (GB); Jonathan Warr, Paris (FR); Catherine Regniez, Paris (FR)

(73) Assignee: Takasago International Corporation, Tokyo (JP)

( * ) Notice: Subject to any disclaimer, the term of this patent is extended or adjusted under 35 U.S.C. 154(b) by 103 days.

(21) Appl. No.: 12/981,988

(22) Filed: Dec. 30, 2010

(65) Prior Publication Data
US 2011/0177995 A1 Jul. 21, 2011

(30) Foreign Application Priority Data
Dec. 31, 2009 (EP) ..................... 09306357

(51) Int. Cl.
*A61Q 13/00* (2006.01)
(52) U.S. Cl.
USPC .......................................... 512/14
(58) Field of Classification Search
USPC ............................................ 512/14
See application file for complete search history.

(56) References Cited

U.S. PATENT DOCUMENTS

| 5,585,343 | A | 12/1996 | McGee et al. |
| 2007/0161526 | A1 | 7/2007 | Vlad et al. |
| 2008/0023569 | A1 | 1/2008 | O'Leary et al. |
| 2008/0311064 | A1 * | 12/2008 | Lei et al. ............... 424/70.11 |

FOREIGN PATENT DOCUMENTS

| EP | 0571677 A1 | 12/1993 |
| WO | 2005/123028 A1 | 12/2005 |

OTHER PUBLICATIONS

Blakeway, J. M., "Water-Based Perfumes", Perfumer & Flavorist, vol. 18, Jan.-Feb. 1993, p. 33-35.
European Search Report issued Jun. 30, 2010, in counterpart European Application No. 09306357.

* cited by examiner

*Primary Examiner* — Ling Choi
*Assistant Examiner* — Lanee Reuther
(74) *Attorney, Agent, or Firm* — Sughrue Mion, PLLC

(57) ABSTRACT

The present invention relates to perfumed composition which comprises: a) from 1% to 25% by weight of a fragrance composition; b) from 1% to 10% by weight of at least one nonionic surfactant having at least two hydrophobic chains each containing from 4 to 20 carbon atoms; c) from 1% to 10% by weight of at least one anionic surfactant having at least two hydrophobic chains each containing from 4 to 20 carbon atoms; d) from 1% to 20% by weight of solvent which is a diol having from 4 to 12 carbon atoms, preferably from 4 to 8 carbon atoms, or a mixture of such diols; e) at least 50% by weight of water.

20 Claims, No Drawings

FRAGRANCE MICROEMULSION COMPOSITIONS

CROSS-REFERENCE TO RELATED APPLICATIONS

This application claims priority from European Patent Application No. 09 306 357.6 filed on Dec. 31, 2009, the entire subject matter of which is incorporated herein by reference.

BACKGROUND OF THE INVENTION

1. Technical Field of the Invention

This invention relates to perfumed, aqueous microemulsion compositions which are low in volatile compounds. These compositions can be used e.g. in fragrances, Eaux de Toilette and cosmetic formulations.

2. Background of the Invention

The need to have cosmetically acceptable, low or zero ethanolic fragrance formulations is due to concerns about volatile organic compounds (VOCs), which are claimed to produce ground level ozone under certain extreme weather conditions. Fragrance compositions such as Eaux de Toilette containing fragrances at levels of 0.5% or above are most commonly solubilised with ethanol. However, ethanol is considered to be a VOC under many current and pending regulations. By "VOC" we mean the Volatile Organic Compounds as defined by the Environmental Protection Agency, and in particular we mean $C_1$-$C_5$ alkanols, such as ethanol, and the more volatile glycols such as ethylene glycol, or 1,2- and 1,3-propylene glycols.

The task of producing low or zero VOC fragrance formulations, which resemble an ethanolic fragrance composition in terms of skin feel, solution clarity, which is storage stable under various conditions such as repetitive freeze thaw cycling, and which exhibits high temperature stability, is difficult. The difficulty increases as the proportion of fragrance within the composition increases. Low VOC fragrance formulations are formulations which are substantially free of ethanol and other solvents classed as VOCs.

Blakeway (Perfumer & Flavorist, 18, January/February, p. 33, 1993) reviews the solution of perfumes using solubilisers, in particular, non-ionic surface active agents. The formulations described by Blakeway require high ratios of surfactant to perfume oil which leave a sticky feeling on the sin and can produce unwanted levels of product foaming.

Microemulsions represent one approach to producing clear, transparent products. For example, U.S. patent application 2008/023569 describes microemulsion compositions including fragrance as the oil phase, anionic and nonionic surfactants together with an ionic solubiliser. European patent application EP-A-571677 relates to clear oil-in-water microemulsions comprising a perfume oil, an aqueous phase and a surfactant, wherein the perfume/surfactant weight ratio is in the range of 0.85 to 2.5. Example 6B shows a microemulsion with a low amount of perfume (0.5 wt %), wherein the weight ratio of nonionic surfactant to anionic surfactant is 50. U.S. Pat. No. 5,585,343 describes low VOC perfume microemulsions comprising a combination of an anionic surfactant and a highly water soluble, hydrophilic coactive solvent such as a glycol or a polyol. International patent application WO 2005/123028 describes fragrance microemulsions comprising a nonionic surfactant, an anionic surfactant and vicinal diol as co-solvent. All the examples use single alkyl chain surfactants.

BRIEF SUMMARY OF THE INVENTION

The present invention provides perfumes aqueous microemulsions compositions which are clear, non-sticky, and are stable over a wide temperature range including freeze thaw recovery. Furthermore, the compositions of the invention do not irritate the skin owing to the nature and level of surfactant used.

This results is achieved by formulating microemulsion compositions containing no more than 20% by weight surfactant, wherein the surfactant comprises specific nonionic and anionic surfactants in a given weight ratio.

The invention encompasses the following embodiments.

(1) A perfumed, aqueous microemulsion composition which comprises:

a) from 1% to 25% by weight of a fragrance composition;

b) from 1% to 10% by weight of at least one nonionic surfactant having at least two hydrophobic chains each containing from 4 to 20 carbon atoms;

c) from 1% to 10% by weight of at least one anionic surfactant having at least two hydrophobic chains each containing from 4 to 20 carbon atoms;

d) from 1% to 20% by weight of solvent which is a diol having from 4 to 12 carbon atoms or a mixture of the diols;

e) at least 50% by weight of water;

wherein the weight ratio of the nonionic surfactant to the anionic surfactant is in the range of from 1:1 to 5:1;

wherein the weight ratio of the fragrance composition to the surfactants is in the range of from 1:2.5 to 2.5:1.

(2) The composition according to (1), wherein the sum of a), b), c), d) and e) is equal to 100%.

(3) The composition according to (1) or (2), wherein the solvent is a diol having from 4 to 8 carbon atoms or a mixture of the diols.

(4) The composition according to any one of (1) to (3), which comprises from 2.5% to 20% by weight of the fragrance composition.

(5) The composition according to (4), which comprises from 5% to 15% by weight of the fragrance composition.

(6) The composition according to any one of (1) to (5), wherein the average ClogP value of the fragrance composition is in the range of from 2.00 to 6.00.

(7) The composition according to (6), wherein the average ClogP value of the fragrance composition is in the range of from 3.00 to 5.00.

(8) The composition according to (6), wherein the average ClogP value of the fragrance composition is in the range of from 3.50 to 4.50.

(9) The composition according to any one of (1) to (8), which comprises from 1% to 5% by weight of each of the nonionic surfactant(s) and the anionic surfactant(s).

(10) The composition according to any one of (1) to (9), wherein the hydrophobic chains of the nonionic surfactant(s) and the anionic surfactant(s) each have from 4 to 16 carbon atoms.

(11) The composition according to (10), wherein the hydrophobic chains of the nonionic surfactant(s) and the anionic surfactants) each have from 4 to 12 carbon atoms.

(12) The composition according to any one of (1) to (11), wherein the solvent is a non vicinal diol or a mixture of non-vicinal diols.

(13) The composition according to (12), wherein the non-vicinal diol is at least one selected from the group consisting of 1,3-butylene glycol, pentylene glycol, hexylene glycol and octylene glycol.

(14) The composition according to any one of (1) to (13), which comprises from 60% to 90% by weight of the water.

(15) The composition according to any one of (1) to (14), wherein the weight ratio of the nonionic surfactant to the anionic surfactant is in the range of from 51:49 to 5:1.

(16) The composition according to (15), wherein the weight ratio of the nonionic surfactant to the anionic surfactant is in the range of from 1.5:1 to 5:1.

(17) The composition according to (15), wherein the weight ratio of the nonionic surfactant to the anionic surfactant is in the range of from 1.5:1 to 4:1.

(18) The composition according to any one of (1) to (17), wherein the weight ratio of the fragrance composition to the total of the surfactants is in the range of from 1:1.5 to 1.5:1.

(19) The composition according to any one of (1) to (18), which further comprises:

f) from 0.5% to 5% by weight of one or more co-surfactants, wherein the co-surfactant(s) represent less than 50% of the total surfactants in the composition.

(20) The composition according to (19), wherein the sum of a), b), c), d), e) and f) is equal to 100%.

DETAILED DESCRIPTION OF THE INVENTION

In a first aspect, the invention relates to a perfumed, aqueous microemulsion composition which comprises:

a) from 1% to 25% by weight of a fragrance composition;

b) from 1% to 10% by weight of a non-ionic surfactant having at least two hydrophobic chains each containing from 4 to 20 carbon atoms;

c) from 1% to 10% by weight of an anionic surfactant having at least two hydrophobic chains each containing from 4 to 20 carbon atoms;

d) from 1% to 20% by weight of solvent which is a diol having from 4 to 12 carbon atoms, or a mixture of the diols;

e) at least 50% by weight of water;

wherein the weight ratio of the nonionic surfactant to the anionic surfactant is in the range of from 1:1 to 5:1;

wherein the weight ratio of the fragrance composition to the surfactants is in the range of from 1:2.5 to 2.5:1;

wherein the sum of a), b), c), d) and e) is equal to 100%.

As used therein, the term "microemulsion" denotes a thermodynamically stable, macroscopically homogeneous mixture of oil, water and surfactant. It contains, on a microscopic level, individual domains of oil and water separated by a surfactant layer. The decisive property is the thermodynamic stability. For a general description of microemulsions and their properties see "Surfactants and polymers in aqueous solution", Jonson B., Lindman B., Holmberg K., Kronberg B., Wiley & Sons Ltd, 1998, 365-399 (incorporated herein by reference).

A microemulsion may be stable over a wide range of temperatures and concentrations with no loss in function or stability. Furthermore, microemulsions may be distinguished from solutions in that they are microstructured and may contain "oil"-swollen micelles, a bi-continuous structure, water-swollen inverse micelles or other structures depending on the amount of "oil" in the system. True solutions show none of these microstructural characteristics. The term "oil" as used in the definition above means the organic, non-surfactant, component of the microemulsion. Generally, microemulsions may show Tyndall scattering and have low interfacial tensions.

Microemulsions have the following identifying characteristics: they are easily prepared by gentle mixing or shaking of the components together; they are thermodynamically stable and will not separate into separate phases or settle out, as long as they retain their chemical identity, without some change in temperature. The formation of a microemulsion may be proved by any one of the following test methods: Tyndall scattering, dynamic light scattering, X-ray scattering, and small angle neutron scattering; all well known scattering techniques. Other important methods include conductivity, NMR and fluorescence techniques described in Surfactant Solutions, New Method of Investigation, R Zana, ed., Marcel Dekker, New York, 1987 and "Microemulsions", Ber. Bunsenges Phys, Chem., 100, 181 (1996) No. 3 (incorporated herein by reference).

As used herein, the term "clear" as applied to microemulsions is intended to mean that the microemulsion when free from any coloring or fluorescent agents has transmittance values of greater than 95%, preferably greater than 99% when measured in a UV/Vis spectrometer at wavelengths of 500 nm, 600 nm, 700 nm, and 800 nm, when measured in a 1 cm cuvette referenced agents demineralised water.

All chemical terms such as functional group names are as generally understood in chemistry and definitions and explanations can be found in "Principles of Chemical Nomenclature A Guide to IUPAC Recommendations" by G. J. Leigh, H. A. Favre, W. V. Metanomski published by Blackwell Science, 1998 [ISBN 0865426865].

In the context of this specification the terra fragrance composition is understood to be synonymous with the terms "fragrance" or "perfume composition" or "perfume" and to refer to mixture of olfactively active materials providing a pleasant smell. The term fragrance ingredient which is also synonymous with the terms "fragrance component", "perfume ingredient" and "perfume component" is taken to mean any individual material which may be an ingredient within the fragrance composition even though that perfume ingredient may itself comprise many individual chemical compounds. This distinction is understood by those familiar with the art of fragrance creation. A perfume ingredient or perfume material can by any natural oil or extract, or chemical compound used in a fragrance composition. Natural oils and extract are described in The Essential Oils by E Guenther published by Van Nostrand (incorporated herein by reference) and may include extracts and distillates from any part of suitable plant: roots, rhizomes, bulbs, corms, stem, bark, heartwood, leaves, flowers, seeds and fruit. Examples of such extracts and distillates include citrus fruit oils such as orange or lemon oil, tree oils such as pine oil or cedarwood oil, herb oils such as peppermint oil, thyme oil, rosemary oil, clove oil or flower extracts such as rose oil, or geranium oil. A wide variety of synthetic odiferous materials are also known for perfumery use, including materials possessing a variety of chemical functional groups, such as acetals, alkenes, alcohols, aldehydes amides, amines, esters, imines, nitriles, ketals, ketones, oximes, thiols, thioletones, etc. Without wishing to be limited, in most cases, fragrance ingredients are odiferous compounds having molecular weights from 70 mass units to 400 mass units to ensure sufficient volatility. Fragrance ingredients will not contain strongly ionizing functional groups such as sulphonates, sulphates, or quaternary ammonium ions. Fragrance ingredients are described more fully in S. Arctander, Perfume Flavors and Chemicals. Vols. I and II, Montclair, N.J., the Merck Index, $8^{th}$ Edition, Merck & Co., Inc. Rahway, N.J. and Allure's Flavor and Fragrance Materials 2008 Published by Allured Publishing Corp ISBN 1-982633-42-1 which are incorporated herein by reference.

In one embodiment, the perfumed, aqueous microemulsion compositions of the invention contain: from 1% to 25% by weight of fragrance composition, preferably they contain from 2.5% to 20% by weight of fragrance composition, more preferably they contain from 5% to 15% by weight of fragrance composition, even more preferably they contain from 8% to 12% by weight of fragrance composition.

It is easier to solubilise more water soluble fragrance molecules than more hydrophobic ones. Water solubility is inversely correlated with the theoretical octanol water partition coefficient usually designated as ClogP. Low ClogP values indicate more water soluble molecules while higher ClogP values are a property of more hydrophobic compounds.

In one embodiment, the average ClogP value of the fragrance composition lies from 2.00 to 6.00; it is preferred if the average ClogP value lies from 3.00 to 5.00 and even more preferred if the average ClogP value lies from 3.50 to 4.50. The average ClogP is calculated by multiplying the ClogP value by the weight percentage of the fragrance in the composition and summing the resultant values.

ClogP refers to the octanol/water partitioning coefficient (P) of fragrance ingredients. The octanol/water partitioning coefficient of a fragrance ingredient is the ratio between its equilibrium concentrations in octanol and in water. The partitioning coefficients of fragrance ingredients are more conveniently given in the form of their logarithm to the base 10, logP. The logP of many fragrance ingredients has been reported; for example, the Pomana92 database, available from Daylight Chemical Information Systems, Inc. (Daylight CIS), Irvine, Calif., incorporated herein by reference, contains many, along with citations to the original literature. However, the ClogP values reported herein are most conveniently calculated by the "Clog" program available within the Chemoffice Ultra Software version 9 available from Cambridge Soft Corporation, 100 Cambridge Park Drive, Cambridge, Mass. 02140 USA or Cambridge Soft Corporation, 8 Signet Court, Swamis Road, Cambridge CBS 8LA UK. The ClogP values are preferably used instead of the experimental logP values in the selection of fragrance ingredients which are useful in the present invention. For natural oils or extracts the composition of such oils can be determined by analysis or using the compositions published in the ESO 2000 date base published by BACIS (Boelens Aroma Chemical Information Service, Groen van Prinsterlaan 21, 1272 GB Huizen, The Netherlands), incorporated herein by reference.

It is also advantageous if the fragrance composition comprises a range of chemical functional groups as it is believed this assists in forming a microemulsion. Theory suggests that fragrance components which possess polar functional groups especially those which are capable of hydrogen bonding such as alcohols and aldehydes will tend to align themselves at the interface of a microemulsion, while compounds without any polar groups, such as hydrocarbons will reside at the centre of the microemulsion droplet. Thus a fragrance which achieves a balance between polar and non polar functionalities will form a microemulsion more readily. Such a balance can be achieved if the fragrance contains from 5% to 60% of hydrocarbon in the fragrance, preferably from 10% to 50% of hydrocarbon and more preferably from 15% to 40% of hydrocarbon.

Fragrance often include solvents which may be used at levels up to 30% of the fragrance. Solvents are defined as relatively low odor liquids which can dissolve target material in reasonable proportions. For perfumery use, solvents may be defined as liquids having sufficiently little odor that they can be added at 30% by weight to a fragrance composition without substantially changing the odor of that composition. Solvents are used in the fragrance industry to dilute olfactively powerful ingredients and to facilitate the handling of solid ingredients by dissolving them and handling them as liquids, Some of the common solvents used in perfumery such as propylene glycol and dipropylene glycol are water miscible; as such they may assist in solubilising a fragrance into a clear aqueous solution or microemulsion. For the purposes of this specification, proportions of fragrance compositions are quoted excluding any water miscible solvent which may be present.

Once formulated into the aqueous microemulsion composition of the invention, the fragrance composition must be stable at 25° C. for 48 hours.

The perfumed, aqueous microemulsion compositions of the invention also comprise a surfactant system containing a nonionic surfactant and an anionic surfactant.

As used herein, the term surfactant means as amphiphilic molecule i.e. containing a hydrophilic and a hydrophobic part which is surface active in that is lowers the surface tension of water and can form sub microscopic molecular assemblies at concentrations exceeding a specific concentration (critical micelle concentration) in aqueous solution. The hydrophilic part of the surfactants may have anionic, cationic, nonionic or zwitterionic chemical functional groups or combinations of these functional groups.

In one embodiment, the surfactant system contains (at least) one anionic and (at least) one non-ionic surfactant each of which must have multiple hydrophobic chains each containing from 4 to 20 carbon atoms (preferably from 4 to 16 carbon atoms, more preferably from 4 to 12 carbon atoms). By multiple hydrophobic chains we mean at least 2 separate linear or branched alkyl, or alkaryl (i.e. an alkyl chain with an aromatic substituent, such as a benzyl group) moieties as shown in the formula 1 or 2 below:

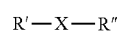
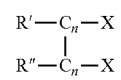

wherein:

X represents any of the common polar hydrophilic groups known in surfactants for example carboxylate, sulphate, sulphonate, sulphosuccinate, glutamate, ethoxylate, propoxylate (or mixtures of two of them) or saccharide group, R' and R" represent linear or branched alkyl, or alkaryl groups each having from 4 to 20 carbon atoms, preferably from 4 to 145 carbon atoms and more preferably from 4 to 12 carbon atoms, and $C_n$ represents from 1 to 3 carbon atoms which link the hydrophobic units with the hydrophilic groups in a Gemini surfactant (the valence requirements on these carbons are satisfied with hydrogen atoms).

For the purposes of this invention, surfactants which have multiple hydrophobic chains that share a common carbon atom such as occurs with branched chain surfactants or due to the polar functionality being covalently bonded part way along an alkyl chain rather than at the terminal carbon atom are not considered to have multiple hydrophobic chains. An example of a surfactant having two chains with a common carbon atom occurs when alcohol ethoxylates are prepared from a secondary alkyl group. Examples of such surfactants include those sold under the Tergital™ brand name.

Surfactants useful in the context of the present invention are those surfactants known as dimeric or gemini surfactants which are defined by having multiple polar groups and multiple hydrophobic groups joined by linking groups either between the polar groups or close to the polar group. The synthesis structures and properties of such surfactants are described in "Gemini Surfactants Synthesis, Interfacial and Solution Phase Behavior and Applications" edited by R Zana and J Xia "Which is Volume 117 in the Surfactant Science Series Published by Marcel Dekker [ISBN 0 8247 4705 4], incorporated herein by reference.

Examples of surfactants suitable for use in compositions of the invention are described in McCutcheon's Surfactants and Detergents, North American & International Editions from MC publishing Glen Rock, N.J. USA which is published annually. The surfactants used are preferably those approved for use in cosmetic and personal core products i.e. they are approved for use under the regulations of the European Union Cosmetics Directive (76/768/EEC) and may be found in Annex II listed under the functions of emulsifying agents, cleansing agents, surfactants, or hydrotropes.

Suitable anionic surfactants which have multiple hydrophobic chains include the dialkyl glutamates, dialkyl phosphates, and the dialkyl sulphosuccinates such as those sold under the Aerosol™ name by Cytec Industries, e.g. sodium diethylhexyl sulphosuccinate sold as Aerosol™ OT.

Suitable nonionic surfactants which have multiple hydrophobic chains include glycerol polyethylene glycol esters, such as those sold under the Cremophor™ name by BASF, e.g. Cremophor™ RH40; dialkyl polyethylene glycols (as shown in formula 1 in which X is a polyethylene glycol having from 5 to 50 repeat units); di- or tri-alkyl sorbitan esters; polysorbates; dialkyl fatty glucamides; di- or higher oligoglycosides; ethoxylated diols such as those sold under the Surfynol™ name by Air Products, e.g. Surfynol™ 465 or Surfynol™ 480.

In one embodiment, the perfumed, aqueous microemulsion compositions of the invention contain from 1 to 10% by weight of each an anionic surfactant and a nonionic surfactant as defined above. In another embodiment, the anionic and nonionic surfactants are incorporated into the microemulsion composition at from 1% to 5% by weight each.

In the context of the present invention, the nonionic surfactant comprises at least 50% of the total surfactant within the microemulsion composition. In one embodiment, the weight ratio of nonionic surfactant(s) to anionic surfactant(s) is in the range of from about 1:1 to about 5:1. In another embodiment, the weight ratio of nonionic surfactant to anionic surfactant is in the range of from about 51:49 to about 5:1. In another embodiment, the weight ratio of nonionic surfactant to anionic surfactant is in the range of from about 1.5:1 to about 5:1. In yet another embodiment, the weight ratio of nonionic surfactant to anionic surfactant is in the range of from about 1.5:1 to about 4:1. In yet another embodiment, the weight ratio of nonionic surfactant to anionic surfactant is in the range of from about 2:1 to about 4:1.

The perfumed, aqueous microemulsion compositions of the present invention may comprise up to 5% by weight, e.g. from 0.5% to 5% by weight, of one or more co-surfactants which improve the solubilizing properties of the primary surfactants. These co-surfactants may be the ionic (cationic, anionic, zwitterionic) or nonionic type, and do not have multiple hydrophobic chains (as opposed to the nonionic and anionic surfactants described above). If used, the co-surfactants(s) represent(s) less than 50% by weight of the total surfactant within the composition. If the co-surfactant(s) used is (are) of the nonionic or anionic type, care must be taken that the weight ratio of nonionic surfactant(s) to anionic surfactant (s) is within the range specified above. In one embodiment, the co-surfactant is a nonionic surfactant.

Example of suitable co-surfactants Include: alkyl glycosides, such as those sold under the Plantacare™ name by Cognis, e.g. $C_{12}$-$C_{16}$ fatty alcohol polyglycoside sold as Plantacare™ 1200UP; mono alkyl sorbitan esters; alkyl ethoxylates; alkyl propoxylates and mixed ethoxy and propoxy ethers in which the hydrophobic unit consists of one alkyl chain of from $C_4$ to $C_{20}$ linear or branched alkyl or alkenyl groups.

The perfumed, aqueous microemulsion compositions of the invention also comprise, as solvent, from 1% to 20% by weight of a diol having from 4 to 12 carbon atoms (preferably from 4 to 8 carbon atoms) or a mixture of the diols. In one embodiment, the microemulsion compositions comprise from 2% to 15% by weight of diol(s). Suitable diols include vicinal diols having from 5 to 8 carbon atoms, such as 1,2-pentanediol, 1,2-hexanediol, 1,2-heptanediol or 1,2-octanediol; and non vicinal diols, i.e. diols with the two alcohol groups on adjacent carbon atoms, having from 4 to 12 carbon atoms, preferably from 4 to 8 carbon atoms, such as 1,3-butane diol (or 1,3-butylene glycol), pentylene glycol, 2-methylpentan-2,4-diol (or hexylene glycol) or octylene glycol. In one embodiment, the did (s) is (are) a non vicinal diol(s).

The properties of the microemulsion compositions of the invention are impacted by the amount of surfactants and solvent. In most cases any reduction in surfactant is only achieved by a large increase in solvent. Moreover an excess of either surfactant or solvent can have adverse affect on the products properties.

Without wishing to be bound by bound by theory we have found that it is possible to formulate aqueous, clear, non-sticky, storage stable, fragrance compositions as microemulsions in which the weight ratio of the fragrance composition to the surfactants is in the range of from 1:2.5 to 2.5:1, preferably in the range of from 1:1.5 to 1.5:1, even more preferably in the range of 1:1.25 to 1.25:1, and especially preferably in the range of 1:1.1 to 1.1:1. Here, the surfactants mean total surfactants in the fragrance composition. In order to achieve the above-mentioned properties, it is advantageous if the weight ratio of the fragrance composition to the solvent is in the range of from 1:3 to 3:1, preferably in the range of from 1:2 to 2:1, more preferably in the range of from 1:1.5 to 1.5:1.

The perfumed, aqueous microemulsion compositions of the present invention comprise at least 50% by weight water. In one embodiment, the compositions comprise from 60% to 90% by weight water. In a further embodiment, the compositions comprise from 70% to 90% by weight water.

Other ingredients that may optionally be present in the compositions of the present invention include for example antioxidants, chelating agents, UV filters, chemaesthetic agents such as cooling agents and preservatives. Additional ingredients such as thickening agents, cosmetic active ingredients, moisturizers, humectants, emollients, opacifiers, pearly gloss impacting substances, pigments, colorants, dyes, antifoams and pH adjusting or buffering agents may also be optionally used in the compositions of the present invention. These ingredients may be added at such point in the process as will be understood by skilled practitioners or as can be determined by a few simple experiments.

The amount of optional ingredients will vary depending on the purpose and effectiveness of the ingredient. Typically, such ingredients represent from 0.0005% to 2.5% by weight, preferably from 0.001% to 1% by weight, more preferably from 0.01% to 0.5% by weight, of the microemulsion composition.

The perfumed, aqueous microemulsion compositions according to the present invention may be prepared, for example, by simple mixing of all the ingredients, for example by hand stirring or if need be, by mechanically mixing (i.e. by some mechanically agitating means) the components of the microemulsion composition, and any optional components, to form a homogeneous mixture.

In one embodiment, the nonionic surfactant is added to the fragrance composition and any oil soluble optional ingredients, and the mixture is stirred. Then the diol or mixture of diols is added with stirring. Separately the anionic surfactant is dissolved or dispersed in water along with any water soluble optional ingredients with warming if necessary. The aqueous solution or dispersion is then added slowly to the organic phase with constant gentle stirring. After the aqueous phase has been added it may be necessary to add a further small amount of diol to ensure absolute clarity.

The invention is illustrated by but not limited to the examples below.

Example 1

A fragrance composition suitable for formulation into an aqueous microemulsion was prepared and contains the following ingredients as shown in Table 1.

TABLE 1

| Ingredient | CAS No. | ClogP | % by wt |
|---|---|---|---|
| Dihydromyrcenol | 18479-58-8 | 3.03 | 25.64 |
| Limonene | 5989-27-5 | 4.35 | 25.64 |
| Methyl dihydrojasmonate | 24851-98-7 | 2.91 | 12.82 |
| Acetyl cedrene | 80449-58-7 | 5.53 | 12.82 |
| Acetyl hexamethyl tetralin | 21145-77-7 | 6.25 | 12.82 |
| Linalyl acetate | 115-95-7 | 3.69 | 6.41 |
| Iso Velvetone | 54464-57-2 | 4.85 | 3.85 |

Example 2

A microemulsion composition was prepared with the following ingredients as shown in Table 2.

TABLE 2

| Ingredient | Function | Phase | % by wt |
|---|---|---|---|
| Fragrance of example 1 | Oil | A | 10 |
| Cremophor RH40[1] | Surfactant | A | 2.50 |
| Aerosol OT[2] | Surfactant | B | 2.50 |
| Plantacare 1200UP[3] | Co-surfactant | B | 2.50 |
| Hexylene Glycol | Solvent | A | 10.00 |
| Water | | B | 72.50 |

[1]PEG-40 Hydrogenated Castor Oil marketed by BASF
[2]Sodium diethylhexyl sulphosuccinate marketed by Cytec Index
[3]$C_{12}$-$C_{16}$ fatty alcohol polyglycoside marketed by Cognis Procedure:

In a beaker equipped with an overhead stirrer and at room temperature, all the ingredients of phase A were mixed. The ingredients of phase B were mixed into the water and stirred until they dissolved. Warming may speed up the dissolution of the Aerosol OT and Plantacare.

With constant low speed stirring phase A was added to phase B. A clear solution was thus obtained.

Measurement of the droplet size of the microemulsion was 0.073 micrometers average particle size determined by laser light scattering.

Comparative Example A

A microemulsion composition was prepared by the procedure described in example 2, using a linear monoalkyl surfactant instead of the diethylhexyl sulphosuccinate.

TABLE 3

| Ingredient | Function | % by weight |
|---|---|---|
| Fragrance of example 1 | Oil | 10 |
| Cremophor RH40 | Surfactant | 2.5 |
| Empicol ESB3M[1] | Surfactant | 2.59 |
| Plantacare 1200UP | Co-surfactant | 2.58 |
| Hexylene Glycol | Solvent | 10 |
| 1,3-Butylene glycol | Solvent | 2.50 |
| Water | | 69.83 |

[1]27% solution of sodium alkyl diethoxy sulphate marketed by Cognis Inc.

On mixing the sample gave a cloudy emulsion which started to separate within a few hours.

Example 3 and Comparative Example B

The microemulsion of example 6B of EP-A-571677 was prepared using the fragrance composition of example 1, and multiplying all the ingredient concentrations, except water, by a factor of about ten, to give a composition with about 5% by weight fragrance (comparative example B). This was compared to the microemulsion of example 2 in which the surfactant concentration was halved and to which 1,3-butylene glycol was added (example 3).

TABLE 4

| Ingredient | Example 3 (% by weight) | Comparative example B (% by weight) |
|---|---|---|
| Fragrance of example 1 | 5.03 | 5.12 |
| Cremophor RH40 | 1.25 | 2.49 |
| Aerosol OT | 1.25 | 0.12 |
| Dehydol 04[1] | | 2.55 |
| Hexylene Glycol | 10.00 | |
| 1,3-Butylene Glycol | 2.51 | |
| Water | 79.96 | 89.72 |

[1]EO(4) octyl alcohol marketed by Cognis Inc.

The microemulsion of comparative example B was more turbid than that of example 3, Measuring the absorption in the visible range at several wavelengths shows a greater degree of scatter for comparative example B.

Example 4

Using the procedure described in example 2, a microemulsion composition was prepared with the following ingredients as shown in Table 5. On mixing a clear solution was obtained.

TABLE 5

| Ingredient | Function | Phase | % by weight |
|---|---|---|---|
| Fragrance of example 1 | Oil | A | 5.04 |
| Surfynol 465[1] | Surfactant | A | 1.25 |
| Surfynol 485[2] | Surfactant | A | 1.25 |
| Cremophor RH40 | Surfactant | A | 2.54 |
| Dioctylsulphosuccinate | Surfactant | B | 2.54 |
| Hexylene Glycol | Solvent | A | 10.00 |
| 1,3-Butylene Glycol | Solvent | A | 2.50 |
| Water | | B | 74.88 |

[1]Ethoxylate [EO(10)] of 2,4,7,9-Tetramethyl-5-decyne-4,7-diol marketed by Air Products Inc.
[2]Ethoxylate [EO(30)] of 2,4,7,9-Tetramethyl-5-decyne-4,7-diol marketed by Air Products Inc.

Example 5

Using the procedure described in example 2, a microemulsion composition was prepared with the following ingredients as shown in Table 6. On mixing a clear solution was obtained.

TABLE 6

| Ingredient | Function | Phase | % by weight |
| --- | --- | --- | --- |
| Fragrance of example 1 | Oil | A | 10.07 |
| Cremophor RH40 | Surfactant | A | 2.50 |
| 1,2-hexane diol | Solvent | A | 10.00 |
| Plantacare 1200UP | Co-surfactant | A | 2.50 |
| Dioctyl sulphosuccinate | Surfactant | B | 2.48 |
| Water | | B | 72.45 |

The invention claimed is:

1. A perfumed, aqueous microemulsion composition which comprises:
    a) from 1% to 25% by weight of a fragrance composition;
    b) from 1% to 10% by weight of at least one nonionic surfactant having at least two hydrophobic chains each containing from 4 to 20 carbon atoms;
    c) from 1% to 10% by weight of at least one anionic surfactant having at least two hydrophobic chains each containing from 4 to 20 carbon atoms;
    d) from 1% to 20% by weight of solvent which is a diol having from 4 to 12 carbon atoms or a mixture of the diols;
    e) at least 50% by weight of water;
    wherein the weight ratio of the nonionic surfactant to the anionic surfactant is in the range of from 1:1 to 5:1;
    wherein the weight ratio of the fragrance composition to the surfactants is in the range of from 1:2.5 to 2.5:1.

2. The composition according to claim 1, wherein the sum of a), b), c), d) and e) is equal to 100%.

3. The composition according to claim 1, wherein the solvent is a diol having from 4 to 8 carbon atoms or a mixture of the diols.

4. The composition according to claim 1, which comprises from 2.5% to 20% by weight of the fragrance composition.

5. The composition according to claim 4, which comprises from 5% to 15% by weight of the fragrance composition.

6. The composition according to claim 1, wherein the average ClogP value of the fragrance composition is in the range of from 2.00 to 6.00.

7. The composition according to claim 6, wherein the average ClogP value of the fragrance composition is in the range of from 3.00 to 5.00.

8. The composition according to claim 6, wherein the average ClogP value of the fragrance composition is in the range of from 3.50 to 4.50.

9. The composition according to claim 1, which comprises from 1% to 5% by weight of each of the nonionic surfactant(s) and the anionic surfactant(s).

10. The composition according to claim 1, wherein the hydrophobic chains of the nonionic surfactant(s) and the anionic surfactant(s) each have from 4 to 16 carbon atoms.

11. The composition according to claim 10, wherein the hydrophobic chains of the nonionic surfactant(s) and the anionic surfactant(s) each have from 4 to 12 carbon atoms.

12. The composition according to claim 1, wherein the solvent is a non vicinal diol or a mixture of non-vicinal diols.

13. The composition according to claim 12, wherein the non-vicinal diol is at least one selected from the group consisting of 1,3-butylene glycol, pentylene glycol, hexylene glycol and octylene glycol.

14. The composition according to claim 1, which comprises from 60% to 90% by weight of the water.

15. The composition according to claim 1, wherein the weight ratio of the nonionic surfactant to the anionic surfactant is in the range of from 51:49 to 5:1.

16. The composition according to claim 15, wherein the weight ratio of the nonionic surfactant to the anionic surfactant is in the range of from 1.5:1 to 5:1.

17. The composition according to claim 15, wherein the weight ratio of the nonionic surfactant to the anionic surfactant is in the range of from 1.5:1 to 4:1.

18. The composition according to claim 1, wherein the weight ratio of the fragrance composition to the total of the surfactants is in the range of from 1:1.5 to 1.5:1.

19. The composition according to claim 1, which further comprises:
    f) from 0.5% to 5% by weight of one or more co-surfactants,
    wherein the co-surfactant(s) represent less than 50% of the total surfactants in the composition.

20. The composition according to claim 19, wherein the sum of a), b), c), d), e) and f) is equal to 100%.

* * * * *